United States Patent [19]
Kirmse et al.

[11] Patent Number: 5,475,884
[45] Date of Patent: Dec. 19, 1995

[54] PATIENT SUPPORT APPARATUS

[75] Inventors: Gerhard Kirmse, Berlin; Ulrich Baer, Neunkirchen; Wolf-Dieter Hildisch, Erlangen, all of Germany; John S. Carey, Jr., Crofton, Md.

[73] Assignee: Siemens Aktiengesellschaft, Munich, Germany

[21] Appl. No.: 93,923

[22] Filed: Jul. 21, 1993

[30] Foreign Application Priority Data

Jul. 21, 1992 [DE] Germany ............... 42 24 036.0

[51] Int. Cl.⁶ .................. A61G 7/10; A61G 7/00
[52] U.S. Cl. .............. 5/601; 5/81.1; 5/600; 378/209
[58] Field of Search ............... 5/81.1, 601, 600, 5/613, 86.1, 83.1; 378/209

[56] References Cited

U.S. PATENT DOCUMENTS

| | | | |
|---|---|---|---|
| 2,681,839 | 6/1954 | Limbach | 5/601 |
| 3,099,020 | 7/1963 | Garfield et al. | 5/620 |
| 3,504,386 | 4/1970 | Rossi | 5/81.1 |
| 3,902,204 | 9/1975 | Lee | 5/81.1 |
| 4,105,923 | 8/1978 | Hynes, Jr. | 5/601 |
| 4,277,218 | 7/1981 | Schweichler | 5/617 |

FOREIGN PATENT DOCUMENTS 3034932  4/1982  Germany.

OTHER PUBLICATIONS

Siemens Sales Brochure "Koordinat Kombi", date unknown.

Primary Examiner—Alexander Grosz
Attorney, Agent, or Firm—Hill, Steadman & Simpson

[57] ABSTRACT

A patient support apparatus comprises a first support plate which can be transferred from an undercarriage onto a table frame of the medical apparatus. The table frame is provided with a second support plate which receives the first support plate directly, but enables an examination subject to be directly received on the second support plate without requiring the assembly of the first support plate.

16 Claims, 4 Drawing Sheets

5,475,884

PATIENT SUPPORT APPARATUS

BACKGROUND OF THE INVENTION

The present invention is directed to a medical device with a patient bearing support apparatus having a first bearing or support plate which is transferrable from an undercarriage onto a table frame of the medical device.

German Published Application 30 34 932 discloses an apparatus having a table frame that is provided with a pedestal supported on the floor, an upper part is height-adjustably seated on the pedestal and is adjustable or movable along its longitudinal axis. An undercarriage is equipped with a bearing or support plate and can be connected to the pedestal so that the support plate can be accepted by the upper part as it is raised by the pedestal. It is known to lock this support plate on the upper part.

A patient lying on the support plate as an examination subject can be moved to the table frame or, for example, a computer tomograph with the assistance of the undercarriage. After the support plate with the patient has been accepted by the upper part of the apparatus, an adjustment thereof into the opening of the computer tomograph is possible for examining the patient. This procedure is particularly advantageous when the patient is severely injured or bed-ridden. When, by contrast, the patients, who are to be examined, can come to the table frame on their own, then the support plate is to be obtained and is to be subsequently mounted on the upper part. It is particularly the acquisition of this support plate and the mounting thereof on the upper part that is time-consuming and work-intensive.

SUMMARY OF THE INVENTION

It is an object of the present invention to provide a medical apparatus with a patient support apparatus comprising a support plate transferrable from an undercarriage onto a table frame of the medical apparatus wherein the preparation for the examination of an examination subject is less time-consuming and work-intensive.

An improvement in a patient support apparatus having a support plate transferrable from an undercarriage onto a table frame of a medical apparatus is achieved by the features that the support plate can be placed onto a support plate of the table frame that directly supports an examination subject and is held by connecting means or locks.

An advantage of the invention is that the examination subjects, for example patients, can independently proceed directly onto the second support plate of the table frame and the patients who are injured or bed-ridden can be brought to the table frame with the assistance of the undercarriage and proceed from there and can be transferred by transferring the first support plate of the undercarriage onto the second support plate of the table frame. The preparation time for examination is, thus, shortened in that no separate support plate must be acquired and is less work-intensive, since one person can initiate the transfer of the first support plate from the undercarriage.

The supports that advantageously comprise means for mechanically locking are provided for positioning the support plates relative to one another so that the support plates can also be pivoted into a slanting position.

Other advantages and features of the invention will be readily apparent from the following description of the preferred embodiments, the drawings and claims.

DESCRIPTION OF THE PREFERRED EMBODIMENTS

Figure 1:
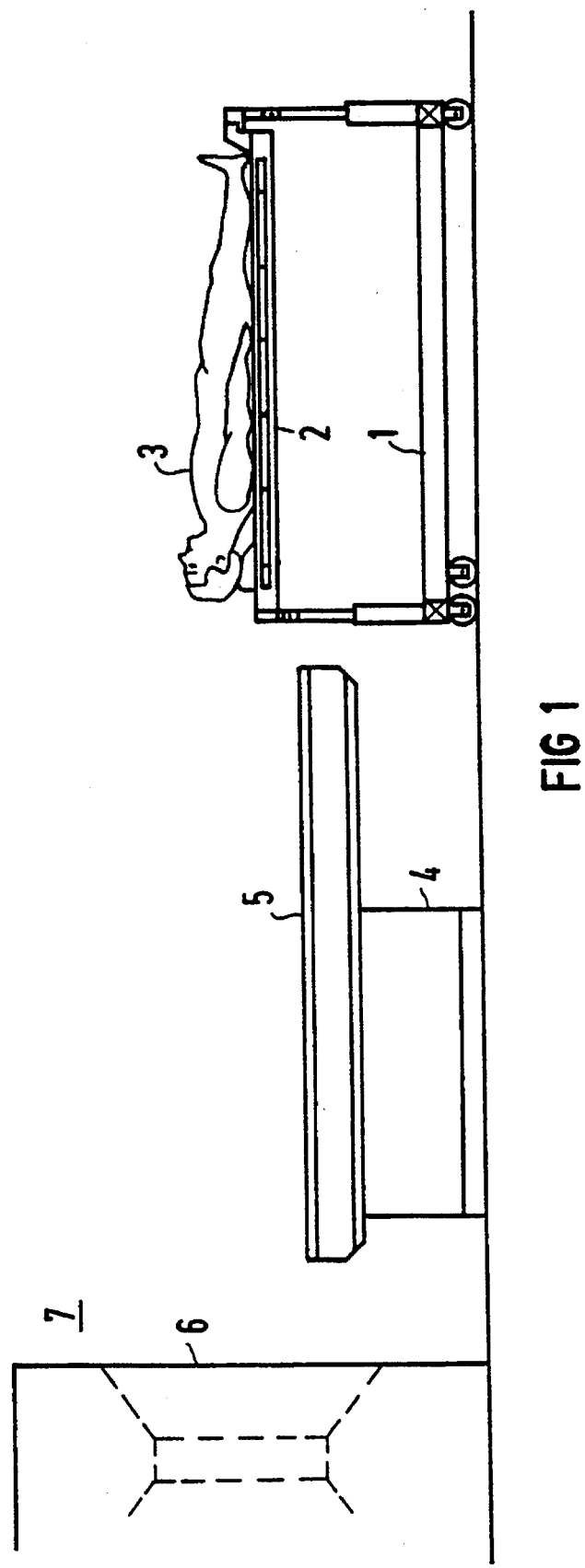
FIG. 1 is a side view of a medical apparatus with the patient support apparatus with the undercarriage being spaced from the support apparatus.

The principles of the present invention are particularly useful when incorporated in a medical apparatus with a patient support apparatus, as illustrated in FIG. 1. The patient support apparatus of FIG. 1 includes an undercarriage 1 which carries a first support plate 2 for an examination subject 3. The examination subject 3 can, thus, be moved via the undercarriage 1 to a table frame 4 of a medical apparatus. The frame 4 includes a pedestal that carries a second bearing or support plate 5 on which the examination subject can be directly placed. The table frame 4 is thereby implemented so that the second support plate 5 having the examination subject situated thereon can be introduced into an opening 6 of a medical apparatus 7, which is only shown schematically and, for example, can be a computer tomograph. Examination subjects, for example patients, can place themselves on the second support plate 5 on their own when they are to be examined. No assistants are required for this purpose. When, by contrast, a severely injured or bed-ridden patient is to be examined, then the patient is moved to the table frame 4 with the assistance of the undercarriage 1, wherein the first support plate 2, together with the patient, can be inventively accepted by the second patient support plate 5. A transfer can occur so that the carriage 1, which has a U-shaped frame, is brought up to the table frame 4 in such a way that the U-shaped frame embraces the table frame 4.

Guide means for this purpose can be provided on the U-shaped frame and, potentially, on the carriage frame 4 so that the undercarriage 1 is arranged in such a position relative to the table frame 4 that the first support plate 2 is now situated over the second support plate 5 and can be transferred thereto. The transfer can occur either in that the first support plate 2 is lowered via a lifting mechanism provided on the undercarriage 1 or in that the second bearing plate 5 is raised by a lifting mechanism arranged in the pedestal of the table frame 4.

Figure 2:
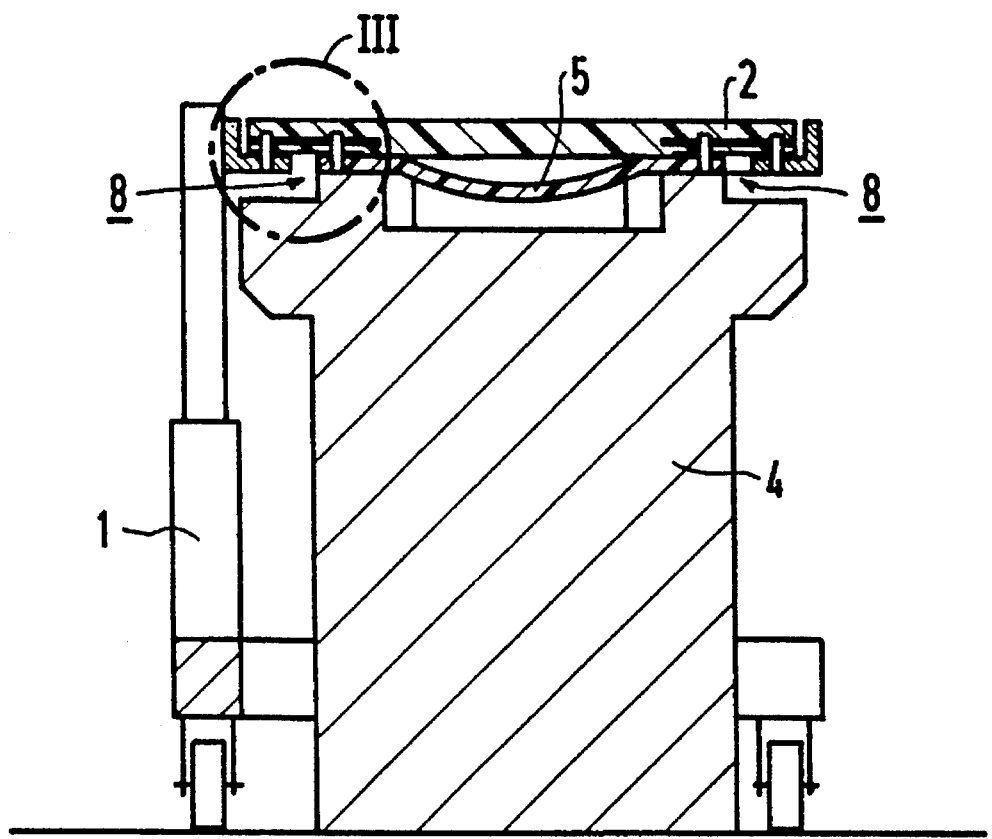
FIG. 2 is a transverse cross sectional view of the patient support apparatus of FIG. 1 with the carriage disposed thereover.

As illustrated in FIG. 2, the first support plate 2 rests on the second support plate 5. Bearings or connecting means 8, for example, which are implemented by using pins engaged in recesses are provided for positioning the supporting plate 2 and, respectively, the supporting plate 5 relative to one another.

After the first support plate 2 has been transferred onto the table frame 4, the undercarriage can be removed so that the patient can be introduced into the opening 6 of the medical apparatus 7 for examination. This movement is that the table frame 4 can adjust the support plates 2 and 5 and move them along their longitudinal axes.

Should it prove necessary for the examination that the support plates 2 and 5 are placed into a slanting position, then it is advantageous when the connecting means comprise means for mechanically locking the support plates 2 and 5 together. Such means are well known to a person skilled in the art and can be implemented as screw-type, snap-in or clamp connections.

Within the framework of the present invention, the medical apparatus can be implemented not only as a computer tomograph but also as an angiography apparatus, an operating table, a magnetic resonance apparatus, a radiation therapy apparatus or as an x-ray diagnostics apparatus.

It is advantageous when the first support plate 2 is entirely composed of a radiation-transmissive material, for example fiber-reinforced plastic or polyurethane rigid expanded plastic. It is self-understood that the bearings or connecting means 8 are also produced of the radiation-transmissive material.

Figure 3:
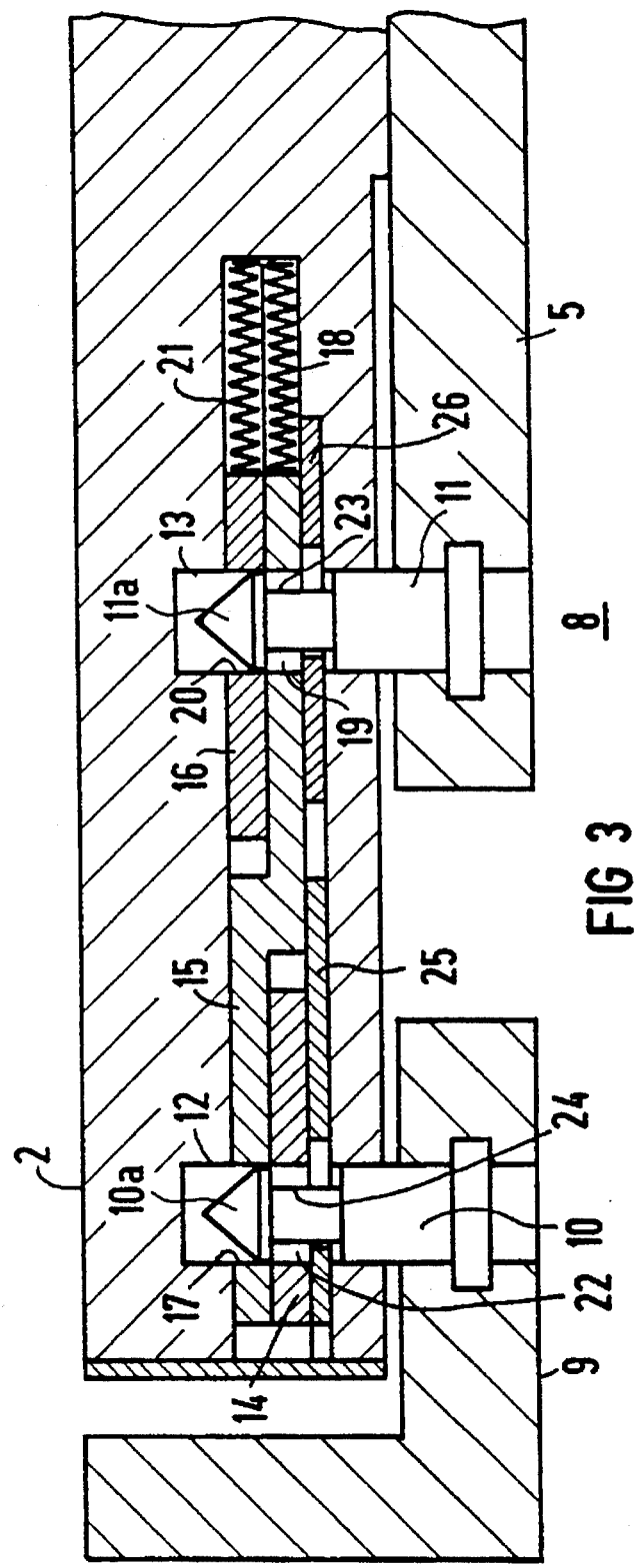
FIG. 3 is an enlarged cross sectional view of the locking mechanism enclosed in a circle III of FIG. 2.

An especially preferred connecting means 8 of the support plates 2 and 5 is schematically shown in FIG. 3. A bracket 9 of the undercarriage 1 has a first pin 10, while the second support plate 5 has a second pin 11. The first support plate 2 has a first recess or bore 12 and a second recess or bore 13 which are spaced apart. The first support plate also has a transverse recess or bore 14 which receives a first interlocking element 15 and a second interlocking element 16, as well as a first safety slide 25 and a second safety slide 26. As illustrated, when positioning the first support plate 2 on the second support plate 5, a conical head 10a of the first pin 10 extends into the recess 12 while a conical head 11a of the second pin 11 extends into the recess or bore 13. In addition, the conical head 10a is received in a first aperture 17 in the first interlocking element 15, and this causes the first interlocking element 15 to be pushed against the spring element 18 to an unlocking position where a second aperture 19 is aligned with the second pin 11. The conical head 11a of the second pin is engaged in the first aperture 20 of the second interlocking element 16 and, as a result thereof, this will position the second interlocking element 16 against the force of a spring element 21 so that the second aperture 22 of the second interlocking element 16 is matched or aligned with the first bore 12.

When the second support plate 5 is lifted, then the first pin 10 will come out of the first recess or bore 12 and also the first aperture 17 so that the locking element 15 is adjusted toward the left by the force of the spring element 18. The second aperture 19 of the first interlocking element 15 then will engage a channel or neck 23 of the second pin to cause an interlocking of the first support plate 2 on the second support plate 5.

When the support plates 2 and 5 are in the arrangement illustrated in FIG. 3 and the first support plate 2 is to be transferred onto the undercarriage when the second support plate 5 is lowered, the second pin 11 will be moved with its conical head 11a out of the aperture 20 so that the interlocking element 16 will be moved to the left by the force of the spring element 21. The second aperture 22 of the second interlocking element 16 is, thus, shifted to engage in a channel or neck 24 of the first pin 10 and, as a result, will interlock the first support plate 2 to the bracket 9 of the undercarriage 1.

Within the framework of the invention, however, the pins can also be provided on the support plate of the undercarriage, and these will then engage into recesses provided in the bracket 9 and/or the support plate 5 of the table frame. Of course, the support plate of the undercarriage can also comprise only one pin that is engaged into a recess or bore of the bracket or, respectively, of the support plate 5 of the table frame.

The interlocking elements 15 and 16 can be implemented as longitudinal slides or rotary slides. The first safety slide 25 will lock the first support plate 2 when the pins 10 and 11 have actuated the interlocking elements 15 and 16 to the position illustrated in FIG. 3. The second safety slide 26 is connected to the second interlocking element 16 and will interlock the plate 5 to the plate 2 by engaging the second pin 11. As illustrated, these safety slides 25 and 26 will be disengaged from their respective pin when the interlocking elements 15 or 16 move to the locking position, respectively.

Figure 4:
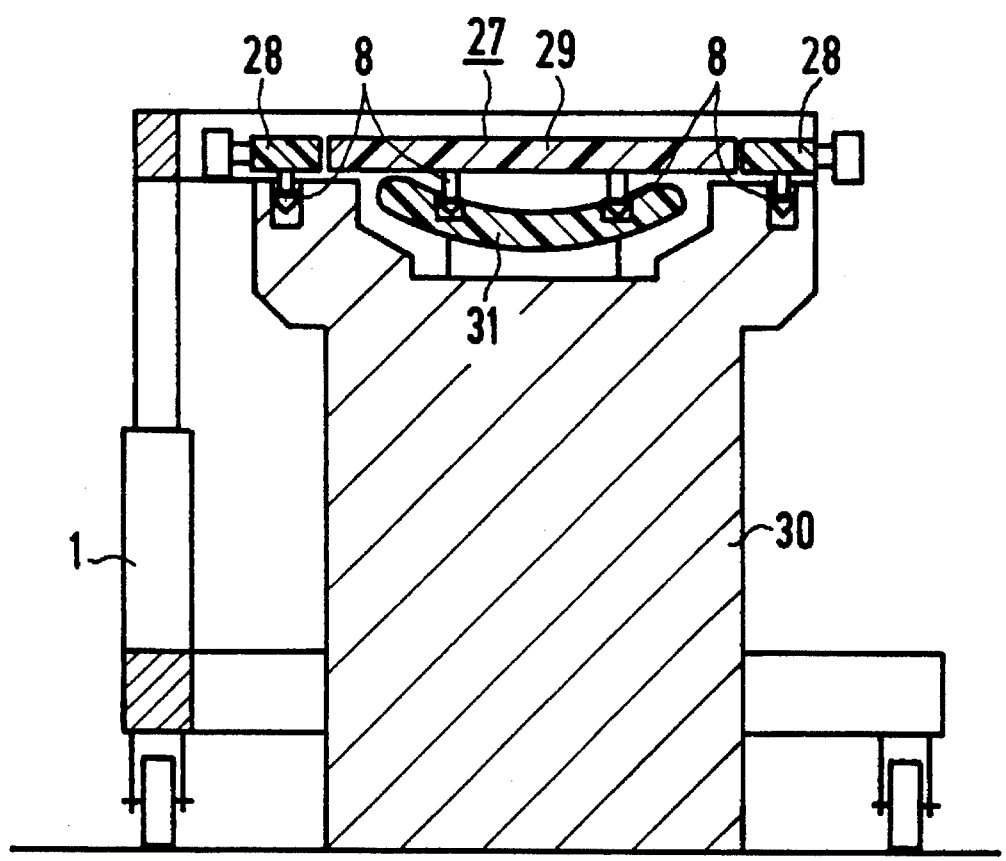
FIG. 4 is a cross sectional view similar to FIG. 2 of a second embodiment of the patient support apparatus of FIG. 1.

An embodiment of the patient support apparatus is shown in FIG. 4. In this embodiment, the first support plate 27 of the carriage 1 is divided in the longitudinal direction by two channels so that it has lateral side portions or parts 28 and a middle or center part or portion 29. As in FIG. 2, the connecting means 8, such as illustrated in FIG. 3, are provided on each of the lateral parts 28 and also the middle or center part 29 and have corresponding locations on the table frame 30 and the second support plate 31. With the connecting means 8, the lateral part 28 can be locked to the pedestal of the table frame 30 and the middle part 29 can be locked to the second support plate 31. The middle part 29 can, thus, be adjusted to move with the second support plate 31 into an opening 6 of a medical apparatus 7, as in the embodiment of FIG. 1. The advantage of this embodiment is that the lateral parts 28 can be manufactured of metal and can, thus, be manufactured in a structurally stable way, while the middle part or center part 29 can be manufactured of lightweight, radiation-transmissive material. The pins of the bearings 8 are preferably provided at the lateral part 28 and also in the center part 29, and these engage into corresponding bores provided in the pedestal of the table frame 30 or of the second support plate 31.

Although various minor modifications may be suggested by those versed in the art, it should be understood that we wish to embody within the scope of the patent granted hereon all such modifications as reasonably and properly come within the scope of our contribution to the art.

We claim:

1. In a medical apparatus having a patient support apparatus having a first support plate transferrable from an undercarriage onto a table frame of a medical apparatus, the improvements comprising the table frame being provided with a second support plate being available for directly supporting an examination subject, said first support plate being placeable on said second support plate, and means for connecting the support plates together so that the examination subject can be either directly supported on the second support plate or directly supported on the first support plate which is supported on said second support plate.

2. In a medical apparatus according to claim 1, wherein the means for connecting comprise means for mechanically locking the support plates together.

3. In a medical apparatus according to claim 2, wherein the means for mechanically locking comprises first and second adjustable interlocking elements being provided on the first support plate, each of said interlocking elements being movable between a first unlocking position and a second locking position, a first pin being fixed on an undercarriage and having a free conical end engageable in a first bore of the first support plate, a second pin being fixed to the second support plate and having a conical end engageable in a second bore of the first support plate, both the first and second adjustable interlocking elements having spaced apertures with a spacing the same as a spacing between the first and second bores of the first support plate, said pins, when inserted in the apertures of said interlocking elements, moving said interlocking elements to the first unlocking position, said pins being structured so that if a first pin is removed from the bore as the carriage is being removed from said support plates, said first pin releasing the first interlocking element to enable it to move to a second locking position engaging the second pin, said second pin, when inserted, holding the second interlocking element in an unlocking position and when the second pin is removed it releases the second interlocking element to move to a locking position on said first pin.

4. In a medical apparatus according to claim 3, wherein each of the first and second interlocking elements include a safety slide movable with the interlocking element to cause interlocking of the pin being inserted through the apertures of said interlocking elements.

5. In a medical apparatus according to claim 1, wherein the first and second support plates are constructed of a material transparent to radiation.

6. In a medical apparatus according to claim 1, wherein the first support plate is sub-divided into a center part and two lateral parts, said lateral parts being connected to the table frame as the centered part is connected to the second support plate.

7. In a medical apparatus according to claim 6, wherein the center part and the second support plate are constructed of a material transparent to radiation and said lateral parts are constructed of a material which is different than the material of the center part.

8. In a medical apparatus according to claim 1, wherein the medical apparatus is a computer tomograph.

9. In a medical apparatus according to claim 1, wherein the medical apparatus is an angiography apparatus.

10. In a medical apparatus according to claim 1, wherein the medical apparatus is an operating table.

11. In a medical apparatus according to claim 1, wherein the medical apparatus is a magnetic resonance apparatus.

12. In a medical apparatus according to claim 1, wherein the medical apparatus is an x-ray diagnostics apparatus.

13. In a medical apparatus according to claim 12, wherein the first and second support plates are constructed of a material transparent to radiation.

14. In a medical apparatus according to claim 1, wherein the medical apparatus is a radiation-therapy apparatus.

15. In a medical apparatus according to claim 14, wherein the first and second support plates are constructed of a material transparent to radiation.

16. In a medical apparatus having a patient support apparatus having a first patient support plate transferrable from an undercarriage onto a table frame of a medical apparatus, the improvements comprising the table frame being provided with a second patient support plate for directly supporting said first support plate; means for connecting the support plates together and the second support plate being able to directly support a patient with the first patient support plate removed.

* * * * *